United States Patent [19]
Cooper

[11] Patent Number: 5,817,611
[45] Date of Patent: Oct. 6, 1998

[54] LAVATORY CLEANSING BLOCKS

[75] Inventor: Nigel Frederick Cooper, Norfolk, England

[73] Assignee: Jeyes Group, PLC, Thetford, England

[21] Appl. No.: 762,157

[22] Filed: Dec. 9, 1996

Related U.S. Application Data

[63] Continuation of Ser. No. 454,258, Jun. 28, 1995, abandoned.

[30] Foreign Application Priority Data

Dec. 3, 1992 [GB] United Kingdom ................... 9225338

[51] Int. Cl.⁶ ............................... C11D 3/20; C11D 3/37; C11D 3/43; C11D 3/395
[52] U.S. Cl. .............................................. 510/192; 510/191
[58] Field of Search ....................................... 510/151, 152

[56] References Cited

U.S. PATENT DOCUMENTS

| | | | |
|---|---|---|---|
| 4,287,080 | 9/1981 | Siklosi | 252/104 |
| 5,205,958 | 4/1993 | Bunczk et al. | 252/102 |
| 5,336,427 | 8/1994 | Bunczk et al. | 252/104 |
| 5,449,473 | 9/1995 | Buuczk et al. | 252/104 |

FOREIGN PATENT DOCUMENTS

| | | |
|---|---|---|
| 341 836 | 4/1989 | European Pat. Off. ........ C11D 3/395 |
| 0 462 643 A1 | 12/1991 | European Pat. Off. . |
| 0 526 437 A1 | 3/1993 | European Pat. Off. . |
| 2061996 | 5/1981 | United Kingdom . |
| WO 92/18605 | 10/1992 | WIPO . |
| PCT/GB93/02352 | 3/1994 | WIPO . |

Primary Examiner—Paul Lieberman
Assistant Examiner—Necholus Ogden
Attorney, Agent, or Firm—Greenlee, Winner an Sullivan, P.C.

[57] ABSTRACT

The invention provides a solid lavatory cleansing block formed of a composition comprising (A) from 5% to 80% by weight of a surface active component comprising one or more anionic surface active agents; (B) from 10 to 75% by weight of a chlorine release agent component consisting of one or more chlorinated cyanuric acid derivatives and chlorine agents; and (C) from 2 to 25% by weight of a solubility control agent (as hereinbefore defined); the composition containing not more than 20% by weight of water-soluble inorganic salt introduced with the anionic surface active agent component and containing no other added fillers or diluents.

8 Claims, No Drawings

LAVATORY CLEANSING BLOCKS

This is a continuation of copending application Ser. No. 08/454,258, filed on Jun. 28, 1995.

This invention is concerned with improvements in and relating to lavatory cleansing blocks.

In particular, the present invention is concerned with solid lavatory cleansing blocks intended to be brought into contact with the flush water of a lavatory or urinal whereby a part of the block is dissolved in the flush water to release active ingredients thereto for cleaning the lavatory or urinal. The blocks are immersed in the water cistern of a lavatory or urinal, either as a free-standing block or may be placed or contained in a dispensing device, to be sited in a lavatory cistern. The invention is also concerned with lavatory cleansing blocks for intermittent contact with the flush water of a lavatory or urinal, e.g., a so-called "rim block" for placing in a container to be held under the rim of a lavatory, or a block to be placed in a container above a cistern for intermittent contact with, e.g. wash water, subsequently fed to the cistern.

One common class of component of lavatory cleansing blocks comprises one or more water-soluble surface active agents. Another desirable component of such blocks would be a halogen release agent, that is a compound which on contact with water releases hypohalous acid and/or hypohalite ions to the water, since these are powerful sanitising and cleansing agents. in principle, there would appear to be no problem in combining these two classes of ingredient in a single block. However, halogen release agents are, by their nature, powerful chemically reactive species, serving as halogenating or oxidising agents. Thus, in practice, we have found that halogen release agents (i) tend to react with surface active materials and/or (ii) tend, when moistened, to evolve gas thereby losing their activity and, in many cases, destroying the physical integrity of the cleansing block. Further, halogen release agents may attack component parts of lavatories, urinals or their cisterns.

A particularly useful class of chlorine release agents comprises the N-chlorinated cyanuric acid derivatives such as sodium dichloroisocyanurate and trichlorisocyanuric acid. We have found in practice, however, that it is generally just not practically possible to reproducibly and reliably incorporate such chlorine release agents in a lavatory cleansing block in amounts sufficient to give useful cleansing and/or sanitising, e.g. amounts of 10% by weight or more.

We have now found, in accordance with the present invention, that the stability of blocks containing chlorinated cyanuric acid derivatives may be improved by incorporating therein a liquid non-oxidisable material. The term "liquid" as used herein is also intended to embrace relatively low melting materials, e.g. having a melting point of less than 60° C., which may become liquified (e.g. due to the action of heat and/or pressure) during the course of manufacture of the block.

According to the invention, therefore, there is provided a solid lavatory cleansing block formed of a composition comprising (A) from 5 to 80%, preferably from 10 to 70%, by weight of a surface active component comprising one or more anionic surface active agents; (B) from 10 to 75, preferably from 15 to 60% by weight of a halogen release agent component, preferably comprising one or more chlorinated cyanuric acid derivative chlorine release agents; and (C) from 1 to 25%, preferably from 4 to 15% by weight of liquid non-oxidisable material.

The block of the invention may also suitably contain a solubility control agent (as hereinafter defined). As discussed below, some of the non-oxidisable liquids may themselves serve as solubility control agents.

Preferably, the blocks of the invention contain no added filler (water-soluble or otherwise) other than that which may be introduced as contaminants or components of a surface active component. Accordingly, the blocks of the invention preferably contain not more than 20% by weight of water-soluble inorganic salts introduced by the anionic surface active agents and contain no added fillers or diluents.

Suitable anionic surface active agents for use in the blocks of the invention include alkali metal, typical sodium, paraffin sulphonates, olefin sulphonates, alkali metal alkyl sulphates and alkali metal alkaryl sulphonates, especially alkali metal benzene sulphonates. A typical example is sodium dodecyl benzene sulphonate which is a readily available material of commerce. The anionic surface active component of the block forms from 5 to 80% by weight of the composition, preferably from 10 to 70% by weight thereof, most preferably from 25 to 65% by weight thereof, and especially from 40 to 60% by weight thereof.

The halogen release component of the block is preferably an N-chlorinated cyanuric acid derivative, such as sodium dichloroisocyanurate or trichloroisocyanuric acid, especially the former. However other halogen release agents, such as calcium hypochlorite, may be employed.

The chlorine release component is present in the blocks of the invention in an amount of from 10 to 75% by weight, preferably from 15 to 70% by weight, more preferably from 20 to 50% by weight, and especially from 30 to 40% by weight.

The third component of the block is the non-oxidisable organic liquid. A wide variety of these may be employed, such as mineral oils, liquid hydrocarbons (e.g. liquid alkanes), chlorinated hydrocarbons, silicone oils, liquid ketones (e.g. 2-decanone), liquid tertiary alcohols (e.g. 2-methyl-hexan-2-ol), and liquid esters [(e.g. simple esters such as methyl decanoate, and more complex esters such as glycerol, propylene glycol, triethylene glycol esters of $C_8$–$C_{10}$ fatty acids and/or succinic acid. Examples of such complex esters are those sold under the trade names Miglyol 812, Miglyol 829, Miglyol 840, Plasthall 4141, Crodamol GTCC, Crodamol PC and Radia 7108.

The non-oxidisable organic liquid is of particular use for blocks intended to be manufactured, stored for use in non-temperate climates. The organic liquid also confers marked advantages for blocks intended for temperate climates. In this latter case, however, more oxidisable components may be present to assist in controlling block life.

A further possible component of the block is a solubility control agent, that is, a compound of lower solubility than the anionic surface active component and which assists in controlling the rate of dissolution of the block.

The solubility control agent may be virtually wholly insoluble in water or if, as discussed below a nonionic surface active agent, have a low HLB, e.g. 5 or less. Such agents should preferably be resistant to attack by the chlorine release component, both in the composition and in aqueous solutions produced by dissolution of the composition in use. It is a. matter of simple experiment to determine whether any candidate is so resistant. Generally, the solubility control agent should be a saturated organic material or a highly chlorinated organic material. Examples of solubility agents which may be employed include polyethylene waxes; fatty alcohols; fatty acids; low ethoxylates (e.g. containing up to 4 ethylene oxide units per mole) of fatty alcohols and alkylphenols; paradichlorobenzene; and difficultly hydrolysable esters such as methyl salicylate and isobornyl acetate.

Certain of the solublility control agents noted above, the ethoxylated fatty alcohols and alkyl phenols, also possess surface active properties and thus may contribute to the overall cleansing effect of a composition containing them. In this connection it may be noted that other nonionic surfactants may be present.

As noted above some of the non-oxidizable liquids may serve as solubility control agents. This is particularly true of the ketonic liquids and the esters, simple or complex. The more complex esters especially, tend to give good results when used as solubility control agents. The effectiveness of the non-oxidisable oils as solubility control agents may be modified, if desired, by using a relatively small amount, e.g. up to about 10% by weight, of another solubility control agent.

The blocks of the invention preferably do not contain more than 20% by weight of inert water-soluble salts, such as sodium sulphate, present as impurities introduced with the anionic surface active agent which is preferably not more than 75% and especially less than 10% by weight thereof. Commercially available anionic surface active agents often contain appreciable amounts of filler or diluent, such as sodium sulphate or sodium phosphate, and such commercially available materials may be used in formulating blocks in accordance with the invention to provided that in so doing too much salt is not introduced. However, in accordance with the invention, substantially no additional (e.g. less than 1% by weight) water-soluble or other filler should be introduced, e.g., sodium sulphate, sodium carbonate, sodium tripolyphosphate, sodium bicarbonate,sodium metasilicate, sodium sesquicarbonate, sodium chloride, clays, calcite or the like.

It may be noted, however, that blocks intended for use in toilets having cisterns in which there is reduced turbulence, e.g. cisterns as found in toilets commonly used on the North American continent, can contain inert fillers in amounts of up to 30% by weight. Indeed, in this case the incorporation of a relatively dense mineral filler, such as calcium sulphate, may well increase the in-use life of the block. Further, the incorporation of certain metal salts, as disclosed for example in EP-A-0341836, can assist in improving stability of the blocks.

As will be appreciated, any other ingredient present in the composition of the invention should be resistant to attack by the chlorine release agent. Thus, for example, most dyestuffs commonly employed in lavatory cleansing blocks to impart a pleasant colouration to the flush water are not sufficiently resistant to the chlorine release agents with the results that (a) the dyestuffs are decolourised or discoloured to an unpleasant colour and (b) available halogen, which would otherwise serve as a sanitizing agent, is lost. However, there are indications that Acid Blue 7 may be adequately resistant. Similarly, most perfumes which are commonly employed in lavatory cleansing blocks are also subject to attack by the chlorine release agents although some odiferous materials may be adequately resistant (and additionally serve as solubility control agents); examples of these being substituted quinolines, cedryl methyl ether and cineole.

Lavatory cleansing blocks commonly contain a germicide or preservative but this is not generally necessary in the case of the blocks of the invention since they already contain powerful germicides, namely the halogen release agents.

As noted above, it is not generally possible to incorporate dyestuffs or perfumes in the blocks of the invention. However, some insoluble pigments are resistant to the chlorine release agents and may be incorporated in the blocks of the invention to impart a colouration to the flush water. Examples of suitable pigments include copper phthalocyanine pigments which can be conveniently incorporated in the blocks of the invention in the forms of dispersions in suitable media.

The blocks of the invention are suitably formed by a compression process, especially an extrusion process comprising the steps of forming a mixture of the components of the composition, extruding this mixture into rod or bar form and then cutting the extruded rod or bar into appropriately sized pieces or blocks. (In this connection it may be noted that a free standing lavatory cleansing block suitably has a weight of from 20 to 200 gms, preferably from 30 to 140 gms).

When producing blocks by an extrusion process it may be advantageous, from the point of view of extended stability of the block, to premix the chlorine release agent and liquid non-oxidisable material, whereby the particles of the chlorine release agent are coated with the non-oxidisable oil. Blocks in accordance with the invention may also be produced by tabletting or by moulding a melt of the ingredients.

When an extrusion process is employed the mixture to be extruded should contain up to 25% by weight, of a liquid component or a solid component which is liquefied under extrusion conditions to act as a processing aid. In the case of the blocks of the invention this is conveniently provided by the use of the non-oxidisable liquid.

The invention also provides a method of cleansing a lavatory by intacting the flush water thereof with a block in accordance with the invention. The invention also provides doses of tablet treatment comprising material having the formulation as described above and in particulate form and contained in a suitable container, e.g. a perforate or water-soluble container.

In order that the invention may be well understood the following examples are given by way of illustration only.

EXAMPLES 1–3

Free-standing lavatory cleansing blocks, each having a weight of about 55 gms, were made up, by extrusion, from formulations comprising 61.5% by weight of sodium dodecyl benzene sulphonate, 30.0% by weight of sodium diisochlorocyanurate and 8.5% by weight of a non-oxidisable oil, namely Miglyol 829 (Example 1), Plasthall 4141 (Example 2) and Crodamol PC (Example 3).

Each of the blocks had an in-cistern life, when tested at a rate of 17 flushes a day, of about 40 days.

EXAMPLES 4–10

Free-standing lavatory cleansing blocks were produced as described in Examples.1 –3 from a mixture comprising 62% by weight of sodium dodecyl benzene sulphonate (Marlon A390), 30% by weight of sodium dichloroisocyanate and 8% by weight of non-oxidisable oil as shown in Table 1 below. The blocks were stored at 37°/75% RH for two weeks and the percentage reduction in available chlorine level measured. The results are0 also shown in Table 1.

TABLE I

| Example | Non-oxidisable oil | % reduction in available chlorine |
|---|---|---|
| 4 | Miglyol 812 | 7.2% |
| 5 | Miglyol 829 Mineral oil (1%) | 10.1% |

TABLE I-continued

| Example | Non-oxidisable oil | % reduction in available chlorine |
|---|---|---|
| 6 | Methyl dodecanate | 0.8% (after 3 weeks) |
| 7 | Decane | 0% (after 3 weeks) |
| 8 | 2-Methyl-hexanol | 11.3% (after 3 weeks) |
| 9 | 2-Decanone | 14.4% (after 3 weeks) |

By way of comparison similar blocks not containing any non-oxidisable oil showed a 41.7% reduction in available chlorine after storage at 37° C. for two weeks.

I claim:

1. A solid lavatory cleansing block formed of a composition comprising:
   (A) from 5–80% by weight of a surface active component comprising one or more surface active agents;
   (B) from 10–75% by weight of halogen release agent component; and,
   (C) from 1–25% by weight of a non-oxidizable material which is liquid or else is liquefiable during manufacture of said block and is selected from the group consisting of liquid ketones, liquid tertiary alcohols and a liquid complex polyfunctional esters derived from polyhydric alchols and mixtures thereof.

2. The lavatory cleansing block of claim 1 further comprising a solubility control agent.

3. The lavatory cleansing block of claim 1 wherein said halogen release agent component comprises one or more chlorinated cyanuric acid derivative chlorine release agents.

4. The lavatory cleansing block of claim 3 further comprising a solubility control agent.

5. The lavatory cleansing block of claim 1 formed of a composition comprising:
   (A) from 10–70% by weight of said surface active component comprising one or more surface active agents;
   (B) 15–60% by weight of said halogen release component;
   and
   (C) from 4–15% of said non-oxidizable material.

6. The lavatory cleansing block of claim 5 further comprising a solubility control agent.

7. The lavatory cleansing block of claim 5 wherein said halogen release agent component comprises one or more chlorinated cyanuric acid derivative chlorine release agents.

8. The lavatory cleansing block of claim 7 further comprising a solubility control agent.

* * * * *

UNITED STATES PATENT AND TRADEMARK OFFICE
CERTIFICATE OF CORRECTION

PATENT NO.   : 5,817,611

DATED        : October 6, 1998

INVENTOR(S)  : Cooper, N.

It is certified that error appears in the above-identified patent and that said Letters Patent is hereby corrected as shown below:

On the title page, item [63], should read:
--Continuation of Ser. No. 454,258, abandoned, filed as PCT/GB93/02352, Nov. 16, 1993--.
in accordance with the recommended presentation, and since the U.S. filing date is not printed, if the application was "filed as" a PCT application.

Signed and Sealed this

Thirtieth Day of May, 2000

Attest:

Q. TODD DICKINSON

*Attesting Officer*   *Director of Patents and Trademarks*